US008263325B2

(12) United States Patent
De Bold (10) Patent No.: US 8,263,325 B2
(45) Date of Patent: Sep. 11, 2012

(54) PREDICTING, DETECTING AND MONITORING TREATMENT OF CARDIOMYOPATHIES AND MYOCARDITIS (75) Inventor: Adolfo J. De Bold, Ottawa (CA)

(73) Assignee: Ottawa Heart Institute Research Corporation, Ottawa, Ontario ( * ) Notice: Subject to any disclaimer, the term of this patent is extended or adjusted under 35 U.S.C. 154(b) by 1308 days.

(21) Appl. No.: 10/712,335

(22) Filed: Nov. 13, 2003

(65) Prior Publication Data
US 2004/0132013 A1 Jul. 8, 2004

Related U.S. Application Data (60) Provisional application No. 60/426,986, filed on Nov. 15, 2002.

(51) Int. Cl.
C12Q 1/00 (2006.01)
G01N 33/53 (2006.01)
G01N 33/567 (2006.01)
(52) U.S. Cl. .................. 435/4; 435/7.1; 435/7.21
(58) Field of Classification Search .............. None
See application file for complete search history.

(56) References Cited

U.S. PATENT DOCUMENTS 5,786,183 A 7/1998 Ryder et al. .............. 435/91.2
6,117,644 A 9/2000 DeBold ...................... 435/7.1

FOREIGN PATENT DOCUMENTS

EP 542255 2/1999
WO WO 97/32900 * 9/1997

OTHER PUBLICATIONS

Bowie et al (Science, 1990, 257:1306-1310).*
Greenspan et al. (Nature Biotechnology 7: 936-937, 1999).*
Lerman et al (Lancet, May 1, 1993, 1105-1109).*
Motwani et al (Lancet, vol. 34, 1 May 1, 1993, 1110-1113).*
Puyo et al (Regulatory Peptides 105, May 15, p. 139-143).*
Marumo et al (Journal of Endocrinology, vol. 119, Issue 1, p. 127-131)(Abstract only).*
Puyo et al (Regulatory Peptides, vol. 105, May 15, 2002, p. 139-143).*
Motwani et al (Lancet, vol. 341, May 1, 1993, 1110-1113).*
Scaglione et al (J Parasitol., Aug; 87(4):923-6).*
Marumo et al (Clinical Chem, 36/9, p. 1650-1653, 1990).*
Marumo et al (Journal of Endocrinology, vol. 119, Issue 1, p. 127-131, 1988) (Abstract only).*
Scaglione et al (The Journal of Parasitology, Aug. 2001, vol. 87, No. 4).*
Piazza et al (Parasitological Research, 80:78-80 1994).*
Ribeiro et al (The Lancet, Aug. 10, 2002, vol. 360, p. 461-462).*
Arad et al (Cardiology, 1996; 87:12-17).*
Totsune et al (Regul. Pept, Jul. 5, 1996;63(2-3):141-7).*
Kaneko et al (Brain Res, May 28, 1993; 612(1-2):104-9)(Abstract only).*

Sudoh et al., Biochem. Biophys. Res. Comm 159:1427-1434 (1989).
Yang-Feng et al., Am. J. Human Genetics 37:1117-1128 (1985).
Altemose et al., "Altered Myocardial Phenotype After Mechanical Support in Human Beings with Advanced Cardiomyopathy" *J. Heart Lung Transplant* 16:765-73, 1997.
Arad et al., "Brain and Atrial Natriuretic Peptides in Patients with Ischemic Heart Disease with and without Heart Failure" *Cardiology* 87:12-17, 1996.
Ationu et al., "Ventricular Expression of Brain Natriuretic Peptide Gene Following Orthotopic Cardiac Transplantation in Children -..." *Cardiovascular Res.* 27:2135-2139, 1993.
Blanche et al., "Heart Transplantation for Chagas' Cariomyopathy" *Ann. Thorac. Surg.* 60:1406-8, 1995.
Carnio et al., "Elevated Levels of Natriuretic Peptides in Lungs of Hamsters with Genetic Cardiomyopathy" *Regulatory Peptides* 70:67-73, 1997.
Davis et al., "Atrial Natriuretic Peptide Levels in the Prediction of Congestive Heart Failure Risk in Frail Elderly" *JAMA* 267:2625-2629, 1992.
Fruhwald et al., "Natriuretic Peptides in Patients with Diastolic Dysfunction Due to Idiopathic Dilated Cardiomyopathy" *E. Heart J.* 20:1415-1423, 1999.
Geny et al., "Transient Reduction Without Normalization of Brain Natriuretic Peptide Early After Heart Transplantation" *J. of Thorac. Cardiovasc. Surgery* 115:473-5, 1988.
Hall et al., "Prognostic Value of N-Terminal Proatrial Natriuretic Factor Plasma Levels Measured Within the First 12 Hours After Myocardial Infarction" *J. Am. Coll. Cardiol.* 26(6):1452-1456, 1995.
Hamada et al., "Increased Plasma Levels of Adrenomedullin in Patients with Hypertrophic Cardiomyopathy: ..." *Clinical Science* 94:21-28, 1997.
Hasegawa et al., "Ventricular Expression of Brain Natriuretic Peptide in Hypertrophic Cardiomyopathy" *Circulation* 88:372-80, 1993.

(Continued)

Primary Examiner — Vanessa L. Ford
(74) Attorney, Agent, or Firm — Fish & Richardson P.C.

(57) ABSTRACT

The present invention provides a method of diagnosing or detecting cardiomyopathies or myocarditis in a patient following an infection. The method comprises obtaining a sample of a biological fluid from the patient, and determining the level of a brain natriuretic peptide (BNP) or a fragment thereof, atrial natriuretic factor (ANF) or a fragment thereof, or both, within the sample of body fluid. The current invention also relates to the monitoring of treatment of cardiomyopathies or myocarditis as a result of an infection, by determining the levels of BNP or a fragment thereof, ANF or a fragment thereof, or both, at one or more than period prior to and optionally subsequent to, treatment. The step of determining the concentration of BNP or ANF involves an assay comprising at least one antibody exhibiting affinity for the BNP or a fragment thereof, ANF or a fragment thereof, and the biological fluid comprises plasma, urine or cerebrospinal fluid. Furthermore, the antibody used within the method may comprise a polyclonal antibody, a monoclonal antibody, or a combination thereof. The method described herein may also involves obtaining at least two samples of body fluid from the patient over a period of time and comparing the BNP, ANF, or both BNP and ANF levels, with a significant decrease of BNP, ANF or both BNP and ANF being indicative of a positive effect of treatment.

19 Claims, 2 Drawing Sheets

OTHER PUBLICATIONS

Hunt et al., "The Amino-Terminal Portion of Pro-Brain Natriuretic Peptide (Pro-BNP) Circulates in Human Plasma" *Biochem. And Biophys. Res. Comm.* 214(3):1175-1183, 1995.

Lerman et al., "Circulating N-Terminal Atrial Natriuretic Peptide as a Marker for Symptomless Left-Ventricular Dysfunction" *Lancet* 341:1109-1113, 1993.

Motwani et al., "Plasma Brain Natriuretic Peptide as an Indicator for Angiotensin-Converting-Enzyme Inhibition after Myocardial Infarction" *Lancet* 341:1109-1113, 1993.

Nishigaki et al., "Marked Expression of Plasma Brain Natriuretic Peptide is a Special Feature of Hypertrophic Obstructive Cardiomyopathy" *J. Am. Coll. Cardiol.* 28:1234-42, 1996.

Puyo et al., "Atrial Natriuretic Factor as Marker of Myocardial Compromise in Chagas' Disease" *Regulatory Peptides* 105:139-143, 2002.

Ribeiro et al., "Brain Natriuretic Peptide and Left Ventricular Dysfunction in Chagas' Disease" *Lancet* 360:461-462, 2002.

Ribeiro et al., "Intermediate Form of Chagas' Disease: Considerations About Diagnosis and Prognosis" *Rev. Soc. Bras. Med. Trop.* 31:301-14, 1998.

Takemura et al., "Ventricular Expression of Atrial and Brain Natriuretic Peptides in Patients with Myocarditis" *J. of Cardiology* 52:213-222, 1995.

Tateyama et al., "Concentrations and Molecular Forms of Human Brain Natriuretic Peptide in Plasma" *Biochem. And Biophys. Res. Comm.* 185(2):760-767, 1992.

Yasue et al., "Localization and Mechanism of Secretion of B-Type Natriuretic Peptide in Comparison with those of A-Type Natriuretic Peptide . . . " *Circulation* 90:195-203, 1994.

Yokota et al., "Dissociation of Cardiac Hypertrophy, Mysoin Heavy Chain Isoform Expression, and Natriuretic Peptide Production in DOCA-Salt Rats" *Am. J. of Hypertension* 8:301-10, 1995.

Mehra et al., "Usefulness of an Elevated B-Type Natriuretic Peptide to Predict Allograft Failure, Cardiac Allograft Vasculopathy . . . " *Amer. J. of Cardiol.* 94:454-458, 2004.

* cited by examiner

SEQUENCE LISTING

```
<160> NUMBER OF SEQ ID NOS: 1

<210> SEQ ID NO 1
<211> LENGTH: 26
<212> TYPE: PRT
<213> ORGANISM: Homo sapiens

<400> SEQUENCE: 1

Lys Ser Arg Glu Val Ala Thr Glu Gly Ile Arg Gly His His Arg Lys Met
1               5                   10                  15

Val Leu Tyr Thr Leu Arg Ala Pro Arg
            20                  25
```

PREDICTING, DETECTING AND MONITORING TREATMENT OF CARDIOMYOPATHIES AND MYOCARDITIS

RELATED APPLICATION INFORMATION

This application claims priority to U.S. Provisional Application Ser. No. 60/426,986, filed Nov. 15, 2002, which is incorporated by reference herein.

The present invention relates to a method for the prediction and diagnosis of heart dysfunction and the monitoring of treatment thereof. More specifically, the present invention relates to a method for the prediction and diagnosis of cardiomyopathies and myocarditis following an infection, and the monitoring of treatment thereof.

BACKGROUND OF THE INVENTION

The cardiac natriuretic peptides (NP) atrial natriuretic factor (ANF) and brain natriuretic peptide (BNP) are polypeptide hormones synthesized, stored and released by cardiac muscle cells (cardiocytes). In many ways, the endocrine heart is a modulator of systems such as the sympathetic nervous system, the renin-angiotensin-aldosterone system and other determinants of vascular tone, extracellular fluid volume and renal function.

ANF and BNP are synthesized by cardiocytes as prepro-hormones that are enzymatically processed to yield prohormones and, ultimately, hormones that are released into the circulation. In humans, the prohormone proANF is a polypeptide that contains 126 amino acids ($ANF_{1-126}$) that is processed to $ANF_{1-98}$ and $ANF_{99-126}$ the latter being the biologically active portion. Human proBNP, on the other hand, is 108 amino acids long and it is processed to $BNP_{1-76}$ and $BNP_{77-108}$ the latter being the biologically active peptide. Both the C-terminal and N-terminal portions of NPs circulate in blood. For example, Hunt et al (1995, *Biochem Biophys Res Comm* 214:1175-1183) report the detection of hBNP and N-terminal ProBNP circulating within human plasma.

Under certain pathophysiological conditions affecting the cardiovascular system, synthesis and release of BNP is significantly augmented. For example, elevated BNP levels have been shown to be elevated in patients with heart failure, in patients exhibiting specific types of cardiomyopathies and in patients exhibiting non-infective myocarditis.

Heart (or cardiac) failure is a pathophysiological state in which the heart is unable to pump blood at a rate commensurate with the requirements of the metabolizing tissues. Increased production of ANF and BNP by the mammalian ventricle is a hallmark of cardiac hypertrophy and failure (Yokota N. et al., 1995 Am. J. Hypertens 8:301-10). Increased levels of BNP have also been observed in patients with heart disease (Tateyama et al., 1992 Biochem. Biophys. Res. Commun. 185:760-7; U.S. Pat. No. 5,786,183; WO 97/32900, all of which are herein incorporated by reference) and it is now known that measurement of the circulating levels of different fragments of these hormones in plasma is a powerful means to identify elderly subjects at risk of heart failure (Davis et al., 1992 *JAMA* 267:2625-2629), establish long term prognosis after myocardial infarction (MI) (Hall et al., 1995 J. Am. Coll. Cardiol. 26(6):1452-1456), stratify patients in terms of response to angiotensin-converting enzyme inhibition post MI (Motwani et al., 1993 Lancet 341:1109-1113) and to demonstrate asymptomatic left ventricular dysfunction (Lerman et al., 1993 Lancet 341:1105-1109; Arad et al., 1996 Cardiology 87:12-17).

Cardiomyopathy is a general diagnostic term designating primary myocardial disease which may progress to heart failure. Cardiomyopathies constitute a group of diseases in which the dominant feature is involvement of the heart muscle itself. In many cases, cardiomyopathies are of obscure or unknown aetiology, but in some cases the cause of the cardiomyopathy is known. For example, inflammatory cardiomyopathies may arise as a result of an infection by a viral, bacterial of parasitic organism. Cardiomyopathies may also result from a metabolic disorder such as a nutritional deficiency or by altered endocrine function. Other cardiomyopathies may be attributed to toxic substances, for example from alcohol or exposure to cobalt or lead. Still other types of cardiomyopathies may result from infiltration and deposition of abnormal cellular materials such as that known to occur during neoplastic infiltration or cardiac amyloidosis.

Elevated BNP levels have been shown to be elevated in specific cardiomyopathies. For example, BNP levels have been shown to be elevated in idiopathic dilated cardiomyopathy (Fruwald et al., 1999 Eur Heart J. 20: 1415-23), hypertrophic cardiomyopathy (Hamada et al., 1997 Clin Sci. (Colch) 94:21-8; Hasegawa et al., 1993 Circ. 88: 372-80), hypertrophic obstructive cardiomyopathy (Nishigaki et al., 1996 J. Am Coll Cardiol. 28:1234-42), dilated cardiomyopathy (Yasue et al., 1994 Circulation 90:195-203; Alterme et al., 1997 J. Heart Lung Transplant 16:765-73), genetic cardiomyopathy (Carnio et al., 1997 Regul Pept. 70:67-73) and in cardiac amyloidosis. However, none of these references disclose that BNP or ANF levels are elevated in inflammatory cardiomyopathies that arise following or as a result of an infection.

Myocarditis is a condition relating to inflammation of the heart muscle. More specifically myocarditis is a disorder caused by inflammation of the myocytes, interstitium, vascular elements or the pericardium of the heart. Much like the cardiomyopathies, the causative agent of myocarditis may be known or unknown. However, it is known that myocarditis may arise as a complication during or after infection by various viral, bacterial or parasitic disease organisms. In North America, viruses (especially enteroviruses) are presumed to be the most common agents of myocarditis, whereas in South America, Chagas disease (American trypanosomia) produced by *Trypanosoma cruzi* is far more common. Patients with myocarditis may exhibit several symptoms including fever, and heart function problems, for example lower cardiac output.

There has been a report suggesting augmented ventricular ANF and BNP expressions in patients with myocarditis (Takemura G. et al., 1995 *Int J Cardiol* 52:213-22:). However the study did not examine serum levels of the peptides, nor was a causative agent identified for the myocarditis. Interestingly, the study also discloses that ANP or BNP-positive myocytes were noted in chronic myocarditis but not in acute fulminant myocarditis or in normal control groups, suggesting that BNP is elevated only in chronic myocarditis and not in acute myocarditis.

The strong correlation between circulating BNP levels and some cardiac diseases has prompted the development of many diagnostic systems to measure BNP levels in patients. WO97/32900 (Mischak RP. et al, published Sep. 12, 1997; which is incorporated by reference) discloses monospecific antibodies to HBNP and their use as diagnostic reagents for the detection of BNP levels in plasma of patients with congestive heart disease. The specific epitopes of the MAb's include fragments of the mature BNP ($BNP_{77-108}$) peptide. These fragments include: 5-13 hBNP, 1-10 hBNP, 15-25 hBNP, and 27-32 hBNP.

EP542255 (Tsuji T. et al. published May 19, 1993; which is incorporated by reference) discloses monoclonal antibodies that recognize the C-terminus of hBNP, and the use of these MAb's within radioimmunoassays (RIA's). The assay involves the determination of hBNP in plasma and can be used for the diagnosis of diseases such as hypertension and altered states of the heart and kidney.

Ationu et al (1993, Cardiovas Res. 27:2135-2139) disclose the monitoring of circulating BNP and ANF levels in paediatric cardiac transplant recipients. In this study increased plasma BNP and ANF levels were noted within patients during the first year after transplant. When BNP levels were re-assayed at 2.5 or 3 years following transplantation, the levels were reduced. Another study (Geny et al., 1988 J Thorac Cardiovas Surgery 115:473-5) considered the relationship between BNP levels before and immediately following heart transplantation, or coronary artery bypass grafting. It was observed that following transplantation, plasma BNP levels, which are typically elevated, decreased and returned to earlier levels. Recently (U.S. Pat. No. 6,117,644), we have demonstrated that circulating BNP levels can be used to monitor cardiac allograft rejection.

Puyo et al (2002, Regulatory Pepides, 105:139-143) analyzed levels of ANF in patients suffering from different stages of Cagas' disease and attempted to determine whether ANF levels can be used to indicate which asymptomatic Chagas patients will develop myocardial disease. This study concluded that ANF levels can not be used to predict development of myocardial disease in asymptomatic patients.

To date, none of the studies described above have suggested that circulating ANF, BNP, or ANF and BNP levels may be used as a predictor or detector of cardiomyopathies and myocarditis that arise following or as a result of an infection. Similarly, none of the studies suggest that circulating ANF, BNP, or ANF and BNP levels may be used to monitor the treatment of such conditions.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to a method for the prediction and diagnosis of heart dysfunction and the monitoring of treatment thereof. More specifically, the present invention relates to a method for the prediction and diagnosis of cardiomyopathies and myocarditis following or as a result of an infection, and the monitoring of treatment thereof.

According to the present invention there is provided a method (Method A) of diagnosing cardiomyopathy or myocarditis within a patient, the method comprising obtaining a sample of a biological fluid from the patient, and determining the level of brain natriuretic peptide (BNP) or a fragment thereof, atrial natriuretic factor (ANF) or a fragment thereof, or both BNP or a fragment thereof and ANF or a fragment thereof, within the sample of body fluid. This invention also relates to the method as described above wherein the step of determining the concentration of BNP, ANF, or BNP and ANF involves an assay comprising at least one antibody exhibiting affinity for the BNP or a fragment thereof, ANF or a fragment thereof, or both BNP or a fragment thereof and ANF or a fragment thereof. Furthermore, this invention is directed to the method as described above wherein the at least one antibody comprises a polyclonal antibody, a monoclonal antibody, or a combination thereof. This invention is also directed to the above method wherein the biological fluid comprises plasma, urine or cerebrospinal fluid.

The present invention also embraces the above method (Method A), wherein the BNP is mature BNP or a fragment thereof, ProBNP or a fragment thereof, or a combination of mature BNP and ProBNP, and where ProBNP comprises $BNP_{1-76}$, $BNP_{1-25}$, or $BNP_{52-76}$ (SEQ ID NO:1), and mature BNP comprises $BNP_{77-108}$, or a combination of two or more of $BNP_{1-76}$, $BNP_{1-25}$, or $BNP_{52-76}$ (SEQ ID NO:1), and $BNP_{77-108}$. Preferably the BNP is $BNP_{7-108}$.

The present invention also embraces the above method (Method A), wherein the ANF is mature ANF or a fragment thereof, ProANF or a fragment thereof, or a combination of mature ANF and ProANF, and where ProANF comprises $ANF_{1-126}$, or a fragment thereof, and mature ANF comprises $ANF_{1-126}$, or a combination of two or more of $ANF_{1-98}$, or a fragment thereof, or $ANF_{1-98}$, and $ANF_{99-126}$. Preferably the ANF is $ANF_{99-126}$.

This invention also relates to the method as defined above (Method A), wherein at least one, or more than one sample of body fluid from the patient is obtained over a period of time, and the levels within the one, or more than one sample are determined and if present compared to determine a change in BNP, ANF or both BNP and ANF levels within the body fluid. Where an increase in BNP, ANF or both BNP and ANF levels over time is an indicator of cardiomyopathy or myocarditis.

Furthermore, this invention is directed to the Method A, as defined above, wherein a decrease in the level of BNP or fragment thereof, ANF or a fragment thereof, or both, is a positive predictor of the efficacy of treatment.

This invention also embraces the method as described above wherein the assay comprising at least one antibody exhibiting affinity for the BNP or a fragment thereof, ANF or a fragment thereof, or both is selected from the group consisting of RIA, ELISA, fluoroimmunoassay, immunofluorometric assay, and immunoradiometric assay, and wherein the assay is performed in the liquid, or solid phase.

The present invention also provides a method (Method B) of monitoring the effectiveness of a therapy for treating cardiomyopathy or myocarditis, comprising determining BNP, ANF or both BNP and ANF levels within a patient over time during the therapy.

The present invention also provides a method (Method C) of monitoring the effectiveness of a therapy for treating an infection which is capable of causing cardiomyopathy or myocarditis, comprising determining BNP, ANF or both BNP and ANF levels within a patient over time during the treatment of the infection.

Further, this invention is directed to a method, either Method B or Method C, as defined above wherein said method comprises obtaining at least two samples of a body fluid from a patient, and determining the level of BNP or a fragment thereof ANF or a fragment thereof, or both, within said two sample of body fluid from the patient, the two samples comprising a first sample and a second sample, the second sample taken subsequent to the first sample and following administration of a therapeutic agent to the patient, and comparing the level of BNP, ANF or both BNP and ANF from the first sample to the level of BNP, ANF or both BNP and ANF in the second sample.

The present invention also relates to a kit which comprises materials to detect and quantify BNP, ANF or both BNP and ANF levels in body fluids. The kit may also comprise materials to detect and quantify the causative agent of the infection.

The present invention also relates to methods and kits as defined above wherein the patient is a human or a non-human animal.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein.

DESCRIPTION OF PREFERRED EMBODIMENT

The present invention relates to a method for the prediction and diagnosis of heart dysfunction and the monitoring of treatment thereof. More specifically, the present invention relates to a method for the prediction and diagnosis of cardiomyopathies and myocarditis following or as a result of an infection, and the monitoring of treatment thereof.

The following description is of a preferred embodiment by way of example only and without limitation to the combination of features necessary for carrying the invention into effect.

Cardiomyopathy is a general diagnostic term designating primary myocardial disease which may progress to heart failure where the dominant feature is involvement of the heart muscle itself. Cardiomyopathies may result from a variety of factors for example:

a metabolic disorder such as a nutritional deficiency or by altered endocrine function;

exposure to a toxic substance, for example from alcohol or exposure to cobalt or lead;

infiltration and deposition of abnormal cellular materials for example, neoplastic infiltration or cardiac amyloidosis; or as a result of an infection by a viral, bacterial of parasitic organism.

Myocarditis is a condition relating to inflammation of the heart muscle. More specifically myocarditis is a disorder caused by inflammation of the myocytes, interstitium, vascular elements or the pericardium of the heart. Much like the cardiomyopathies, the causative agent of myocarditis may be known or unknown. For example, myocarditis may arise as a complication during or after infection by various viral, bacterial or parasitic disease organisms. In North America, viruses, especially enteroviruses, or other agents, for example rickettsial, bacterial, mycobacterial, spirochetal or fungal infections. are presumed to be the most common agents of myocarditis, whereas in South America, Chagas disease (American trypanosomia) produced by *Trypanosoma cruzi* is far more common.

An aspect of the present invention as disclosed herein relates to the determination of plasma levcels of BNP, or a fragment of, levels in diagnosing and predicting cardiomyopathies and myocarditis following an infection or as a result of an infection. Another aspect of the present invention relates to the determination of levels of BNP or a fragment thereof, at various times following administration of a therapeutic agent for treating the cardiomyopathy or myocarditis or infection which precedes or results in the cardiomyopathy or myocarditis such that the effectiveness of therapy may be followed.

Furthermore, the present invention relates to the determination of plasma ANF, or a fragment thereof, levels in diagnosing and predicting cardiomyopathies and myocarditis following an infection or as a result of an infection, as well as the determination of levels of ANF or a fragment thereof, at various times following administration of a therapeutic agent for treating the cardiomyopathy or myocarditis or infection which precedes or results in the cardiomyopathy or myocarditis such that the effectiveness of therapy may be followed.

The present invention also pertains to determining plasma levels of BNP or a fragment thereof, ANF or a fragment thereof, or both BNP or a fragment thereof and ANF or a fragment thereof, in diagnosing and predicting cardiomyopathies and myocarditis following an infection or as a result of an infection. Another aspect of the present invention relates to the determination of levels of BNP or a fragment thereof, ANF or a fragment thereof, or both BNP or a fragment thereof and ANF or a fragment thereof at various times following administration of a therapeutic agent for treating the cardiomyopathy or myocarditis or infection which precedes or results in the cardiomyopathy or myocarditis such that the effectiveness of therapy may be followed.

As used herein, ProBNP refers to the entire 1-108 amino acid sequence of the brain natriuretic peptide, and it is also referred to as $BNP_{1-108}$. Specific fragments of BNP are referred to based on the numbering of the ProBNP molecule. For example, the mature, 32 amino acid, active BNP portion is referred to as $BNP_{77-108}$, other fragments used within this invention include the N-terminal portion of ProBNP, for example, which is not to be considered limiting in any manner, $BNP_{1-25}$, and the C-terminal region of the cleaved portion of BNP, for example but not limited to, $BNP_{52-76}$ (SEQ ID NO:1), derived from the N-terminal region of ProBNP. However, other portions of the ProBNP or BNP molecule may also be suitable for the method of this invention and may be readily determined by one of skill in the art.

A similar nomenclature is used with regards to ANF. The entire ProANF is $ANF_{1-126}$, while specific portions of this peptide are numbered with reference to the ProANF molecule. These fragments include, but are not limited to, $ANF_{1-30}$, $ANF_{74-98}$, $ANF_{99-126}$. It is to be understood that other portions of the ProANF or ANF molecule may also be suitable for the method of this invention and may be readily determined by one of skill in the art.

BNP and ANF peptides, or fragments thereof, are detectable within biological fluids, for example plasma, urine and cerebrospinal fluid. The occurrence of these peptides or associated fragments can readily be determined within these biological fluids following the method of this invention as well as using methods known to one of skill in the art. Non-limiting examples of such methods include U.S. Pat. No. 6,117,644; EP 542 255; WO 97/32900 (which are incorporated herein by reference)

In the context of this invention, methods for the detection of BNP or ANF may include a variety of known techniques that would be evident to one of skill within the art. Such methods include but are not limited to radioimmunoassay (RIA), enzyme-linked immunosorbant assay (ELISA), and other immunological-based assays, including fluoroimmunoassay, immunofluorometric assay, and immunoradiometric assay, involving radioactive tracers, colorometric, fluorogenic or enzymatic markers, or chemical luminescence, or immunoturbimetry (e.g. U.S. Pat. No. 6,117,644; WO97/32900; Mischak R P. et al, published Sep. 12, 1997; EP542 255; Tsuji T. et al. published May 19, 1993; which are incorporated by reference). These immunological assays may involve the use of either polyclonal or monoclonal antibodies, or a combination thereof, that recognize specified portions of either BNP or ANF.

Based upon the results presented below, there is no specific portion of BNP or ANF that is preferred in order to generate these polyclonal or monoclonal antibodies for the purposes of this invention. Rather, any fragment of ProBNP (i.e. $BNP_{1-108}$) or ProANF ($ANF_{1-126}$), may be used for the preparation of antibodies and be suitable for detecting natriuretic peptide (NP levels). Several of these peptides are also available commercially (e.g. Advanced ChemTech). The antibodies so prepared may be used for the detection of ANF or fragments thereof, or BNP or fragments thereof, or a combination of both ANF and BNP, or a combination of the fragments of ANF or BNP, using the methods as described herein.

As a result of the high degree of correlation between the cleaved N-terminal and C-terminal portions of the cleaved portion of the peptide and the mature peptide in plasma, and as a result of the high levels of these peptides within plasma, the detection of any portion of the BNP or ANF peptide may be assayed for in the current invention.

Infections Associated with Cardiomyopathy or Myocarditis

By the term infection it is meant any viral infection, rickettsial infection, bacterial infection, mycobacterial infection, spirochetal infection, fungal infection, parasitic infection or any other infection by any other infectious organism known in the art. The infection may directly cause cardiomyopathy or myocardits, or the infection may indirectly contribute to the development of cardiomyopathy or myocarditis.

Chagas disease is an insect-transmitted parasitic disease common in South and central America. Chagas disease is caused by *Trypanosma cruzi*, a parasite related to the African trypanosmae that causes sleeping sickness. It is spread by several families of blood sucking insects such as Rhodnius, Panstrongylus, and Triatoma and is a major health problem in South America. Chagas disease affects both humans and animals.

Chagas disease has an acute phase and a chronic phase. The acute phase may exist without symptoms or have very mild symptoms such as swelling and discoloration at the site of infection where the blood-sucking insect caused the initial infection. As the parasite spreads from the bite site, the patient often develops fever, malaise and swelling of the lymph nodes. The liver may become enlarged and abnormal or rapid heart rhythms develop in half of the patients. Approximately 1 in 10 infected people die during the acute phase.

The disease may go into remission after the acute phase and may become chronic with no further symptoms for many years. When symptoms finally develop, they appear as cardiomyopathy or myocarditis, which may progress to heart disease. Death is usually from heart disease.

A recent report suggests that heart transplantation is a reasonable therapeutic option for patients with end-stage Chagas cardiomyopathy (Blanche et al., Ann Thorac. Surg. 60: 1406-8). Further, the absence of clinical, radiological, and electrocardiographic manifestations of cardiac involvement in *Trypanosoma cruzi* infected individuals at early stages presents a significant limitation to treating those individuals. When submitted to advanced cardiovascular tests, these patients may present significant abnormalities (Ribeiro and Rocha, 1998 Rev. Soc. Bras Med Trop. 31:301-14). However, these advanced tests can be expensive and not readily attainable by infected individuals.

As described herein, circulating BNP, ANF, or both BNP and ANF levels may be used as a predictor or a diagnostic tool to detect cardiomyopathy or myocarditis in patients exhibiting symptoms associated with infections, for example but not limited to, Chagas disease (the cardiomyopathy or myocarditis often termed chagasic cardiopathy, chagasic myocardiopathy or chagasic myocarditis). Similarly, circulating BNP, ANF, or both BNP and ANF, levels also provide a way to monitor various types of therapy for treating cardiomyopathy and myocarditis as a result of an infection. Further, the circulating BNP, ANF, or both BNP and ANF levels provide a way to monitor various types of therapy for cardiomyopathy or myocarditis resulting from an infection for example but not limited to, Chagas disease, in human and nonhuman animals.

Figure 1:
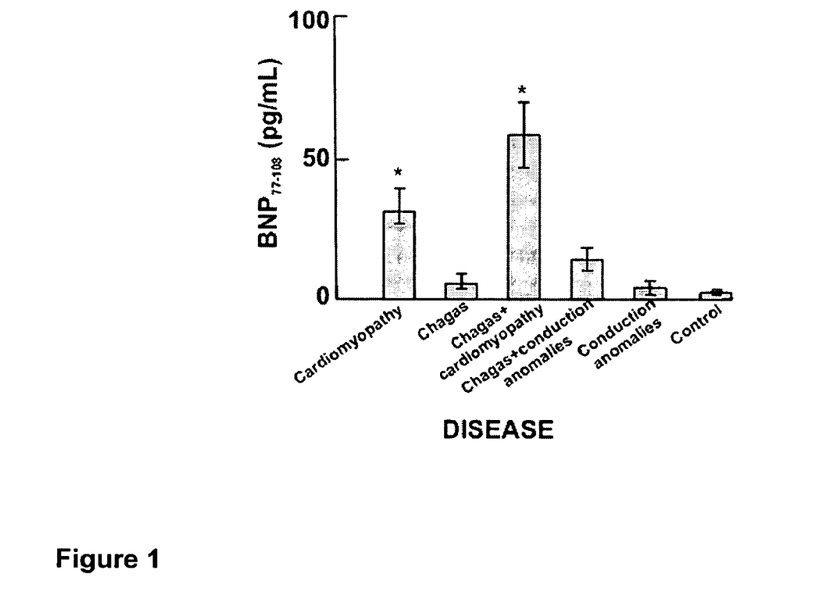
FIG. 1 shows the levels of serum $BNP_{77-108}$ for patients exhibiting a cardiomyopathy, Chagas disease, Chagas disease and a cardiomyopathy, Chagas disease and conduction abnormalities, conduction abnormalities alone and a control group. The Y-axis has units of pg/ml.

FIG. 1 shows the relative $BNP_{77-108}$ levels circulating in patients exhibiting general non-chagasic cardiomyopathies, Chagas disease, Chagas disease and chagasic cardiomyopathy, Chagas disease also having conduction abnormalities within the heart, conduction abnormalities, and a control group. Even though $BNP_{77-108}$ levels are shown in FIG. 1, other fragments of BNP may be used for this determination.

Patients infected with Chagas disease and also exhibiting chagasic cardiomyopathy show significantly elevated serum levels of BNP relative to all the other groups. Furthermore, patients in the early stages of Chagas disease, that is where the disease has not progressed far enough to exhibit clinical signs of chagasic cardiomyopathy or myocarditis show slightly elevated BNP levels compared to the control group, yet these BNP levels are significantly reduced compared to the disease-infected and cardiomyopathy-exhibiting group.

Patients exhibiting general cardiomyopathies or non-chagasic cardiomyopathies also display an elevated serum BNP level, however, these levels are much lower than the BNP levels of patients infected with Chagas disease and also exhibiting chagasic cardiomyopathy. Two other control groups, the first comprising patients exhibiting general conduction abnormalities within the heart and the other comprising patients with both Chagas disease and conduction abnormalities also display somewhat elevated serum BNP levels compared to the control group.

These results indicate that the BNP levels increase early in Chagas disease. The involvement of the heart muscle in the disease and the development of a cardiomyopathy or myocarditis is accompanied by a significant elevation in circulating BNP levels. Thus, BNP levels may be used to detect or predict the onset or development of cardiomyopathy or myocarditis following or as a result of an infection. Further, the levels of BNP may be used to monitor the effectiveness of treatment of the cardiomyopathy or myocarditis, as therapeutic agents which effectively treat cardiomyopathy or myocardits may reduce the level of BNP circulating within patients. The levels of BNP may also be used to monitor the effectiveness of therapy for Chagas disease, especially in later stages of the disease when levels of BNP are significantly elevated compared to non-infected individuals. Erradication of the *Trypanosoma cruzi* organism from a patient may also be associated with an improvement in the cardiomyopathy or myocardits and a reduction in circulating BNP levels.

Figure 2:
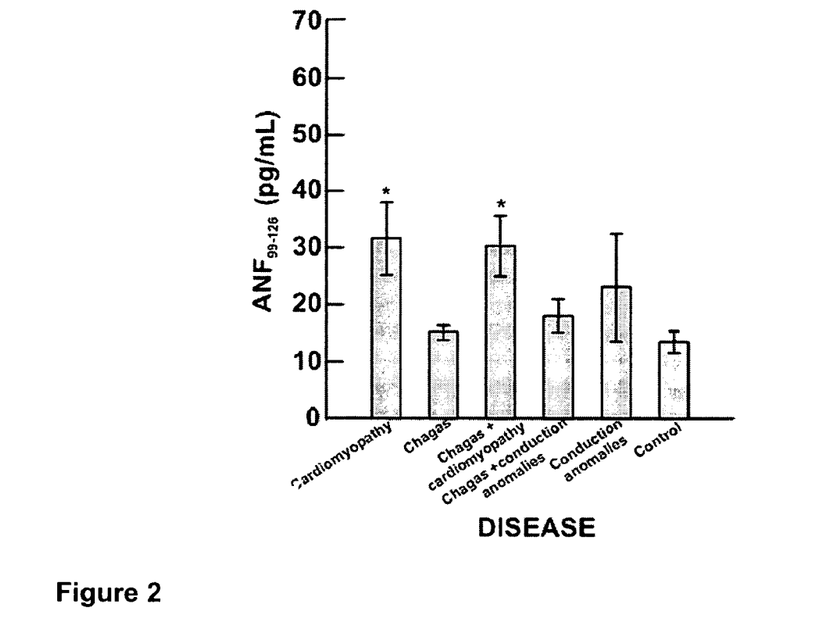
FIG. 2 shows the levels of serum $ANF_{99-126}$ for patients exhibiting a cardiomyopathy, Chagas disease, Chagas disease and a cardiomyopathy, Chagas disease and conduction abnormalities, conduction abnormalities alone and a control group. The Y-axis has units of pg/ml.

FIG. 2 shows the relative levels of $ANF_{99-126}$ circulating in patients exhibiting general nonchagasic cardiomyopathies, Chagas disease, Chagas disease and chagasic cardiomyopathy, Chagas disease also having conduction abnormalities within the heart, conduction abnormalities, and a control group. As shown in FIG. 2, patients displaying non-chagasic cardiomyopathies have elevated serum levels of $ANF_{99-126}$ relative to the control group. Patients infected with Chagas disease show similar serum levels of $ANF_{99-126}$ to the control group while patients with Chagas disease and chagasic cardiomyopathy display elevated levels compared to the control group. Similarly patients exhibiting Chagas disease plus conduction abnormalities or conduction abnormalities alone also display higher levels of $ANF_{99-126}$ compared to the control group.

Collectively, this data suggests that BNP, ANF, or both BNP and ANF levels may be used to aid in the prediction, detection, and monitoring of cardiomyopathy and myocarditis in patients exhibiting symptoms associated with infection. BNP levels may be a more sensitive indicator than ANF, however, ANF levels may be useful in combination with BNP levels to provide additional information regarding the disease state and may make it possible to make more accurate predictions or diagnoses. Furthermore, both the levels of ANF and BNP may be assayed simultaneously to provide for more refined monitoring of the disease and its symptoms.

Therefore, the present invention provides a method of assisting in the diagnosis of cardiomyopathy, myocarditis, or both, in a patient comprising:
 i) obtaining a sample of a body fluid from the patient, and
 ii) determining a level of a brain natriuretic peptide (BNP) or a fragment thereof, atrial natriuretic peptide (ANF) or a fragment thereof, or both BNP and a fragment thereof and ANF or a fragment thereof, within the sample; and
 iii) comparing the level of BNP, ANF or both BNP and ANF to the level of BNP, ANF, or both BNP and ANF with that determined from a separate sample obtained from a control group,
where an increase in the level of BNP, ANF, or both BNP and ANF in the sample, compared to the level of BNP, ANF, or both BNP and ANF in the control group, is an indicator of a symptom of cardiomyopathy, myocarditis or both cardiomyopathy and myocarditis.

The current invention allows therapeutic intervention and monitoring of the effectiveness of therapy relatively early in the disease. Further, the detection systems for BNP are easy to use and are relatively inexpensive, allowing these tests to be easily implemented in developing countries.

The present invention is not limited to predicting, detecting, and monitoring cardiomyopathy or myocarditis in patients with Chagas disease. Any infective disease which results in cardiomyopathy or myocarditis may be subject to the present invention. Examples include but are not limited to viral infections such as enteroviruses, rickettsial, bacterial, mycobacterial, spirochetal or fungal infections. Also, the present invention is directed to human patients and non-human patients capable of being infected by an infection. As would be known by one skilled in the art, the infection in a human or non-human patient must be associated either directly or indirectly with the cardiomyopathy or myocarditis.

The present invention also provides a method of monitoring the effectiveness of a therapy for treating cardiomyopathy, myocarditis, or an infection capable of causing cardiomyopathy or myocarditis in a patient, the method comprising;
 i) obtaining two or more than two samples of a body fluid from the patient over a period of time; and
 ii) determining the level of a brain natriuretic peptide (BNP) or a fragment thereof, atrial natrieuretic peptide (ANF), or a fragment thereof, or both BNP or a fragment thereof and ANF or a fragment thereof, within the two or more than two samples of body fluid,
where, a decrease in BNP, ANF or both BNP and ANF in the sample over the period time is an indicator of success of the treatment.

Any suitable period of time may be selected to monitor effectiveness of therapy. An non-limiting example of the period of time between obtaining samples may be between about 1 to about 30 days, preferably, between about 2 and about 10 days, more preferably about 3 to about 5 days.

As one skilled in the art will appreciate, there can be significant differences between BNP levels in control groups from different populations. These differences may be attributable to slight variations in the genetic makeup of individuals from distinct populations and on environmental factors which may further influence these variations. For example, but not wishing to be limiting a control group comprising individuals from a South American population may have significantly different circulating BNP levels from a control group comprising a North American population. Therefore it is preferable that the patients being tested or monitored for cardiomyopathies or myocarditis as a result of an infection are compared with a proper control group. A proper control group would be known to one skilled in the art.

The present invention also relates to a kit for measuring and quantifying BNP levels. The kit may comprise one or more than one antibody to BNP or a fragment thereof, one or more than one antibody to ANF or a fragment thereof, or antibodies to both BNP or a fragment thereof, and ANF or a fragment thereof, optionally solutions for antibody determination, and instructions for use. The kit may also comprise a system for identifying and quantifying the infection using any means known in the art, for example, but not limited to antibody based assays.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

Examples

Subjects

A total of 52 subjects were studied. Based on clinical criteria, electrocardiographic, echocardiographic and serology status the patients were divided into 5 groups: 1. Patients having Chagas disease with no evident myocardial involvement (Chagas, n=11). 2. Patients having a cardiomyopathy of origin other tha from Chagas disease (Cardiomyopathy, n=8). 3. Patients having a cardiomyopathy associated with Chagas disease (Chagas+cardiomyopathy, n=10). 4. Patients having conduction anomalies but no Chagas disease (Conduction anomalies, n=6), and, 5. Patients with Chagas disease that presented conduction anomalies only (Chagas+conduction anomalies, n=9).

Radioimmunoassay Peptides

Figure 3:
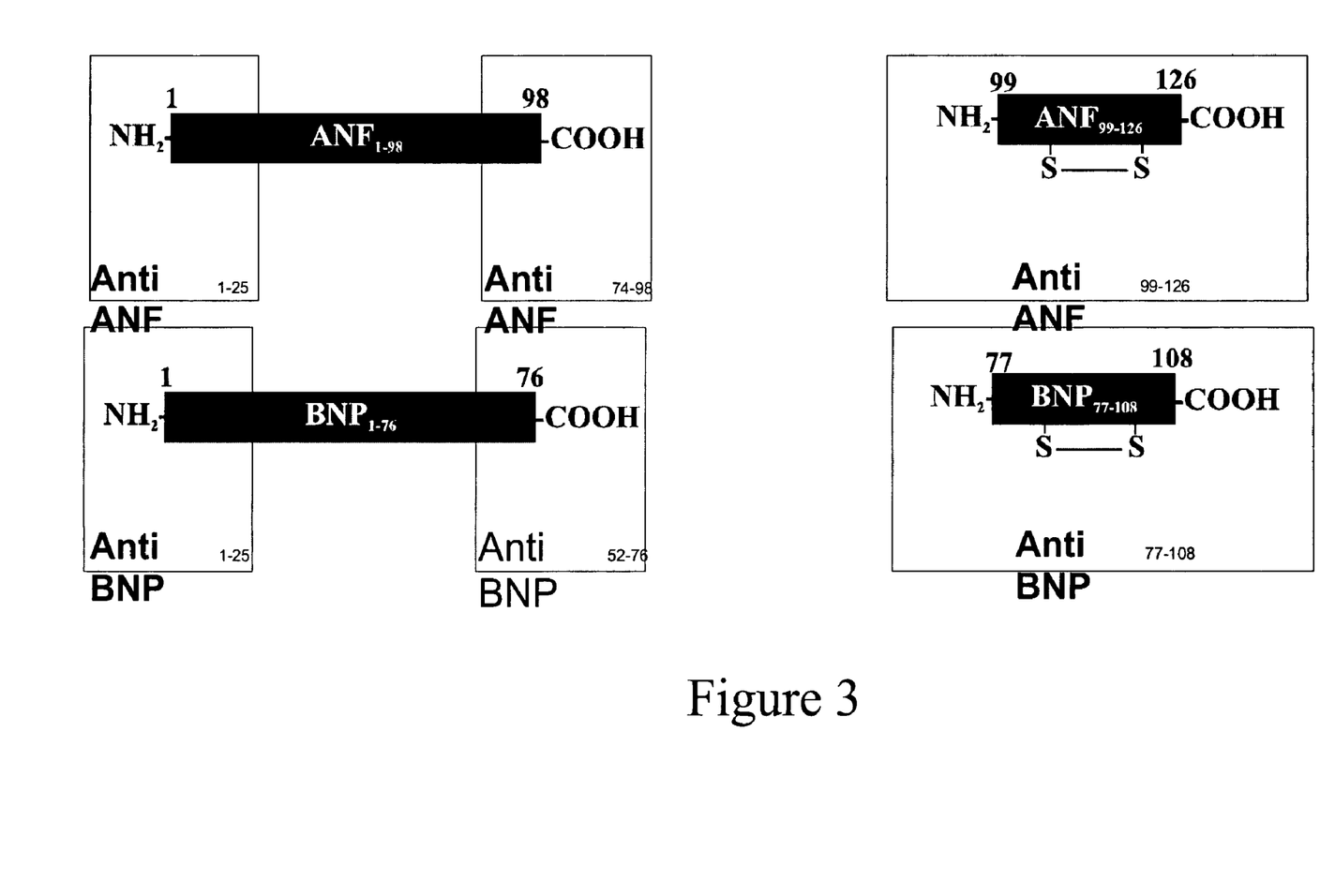
FIG. 3 shows peptide regions used to prepare standard curves and develop antibodies.

Peptides to develop antibodies and to construct standard curves for the radioimmunoassay procedure were custom synthesized commercially. Antibodies were developed against $ANF_{1-25}$, $ANF_{74-98}$, $ANF_{99-126}$, $BNP_{1-25}$, $BNP_{52-76}$ (SEQ ID NO:1), and $BNP_{77-108}$. Peptides regions used to construct standard curves and develop antibodies are depicted in FIG. 3 with sequence numbering derived from the peptide prosequences.

Production of Monoclonal Antibodies

Synthetic $ANF_{1-25}$, $ANF_{74-98}$, $ANF_{99-126}$, $BNP_{1-25}$, $BNP_{52-76}$ (SEQ ID NO:1), and $BNP_{77-108}$ are produced and each are separately coupled to bovine thyroglobulin using the carbodiimide method (Skowsky W R et al. 1972, J Lab Clin Med 80:134-144, which is incorporated herein by reference) to form corresponding antigen-thyroglobulin conjugates. Female BALBoC mice are separately immunized with each antigen-thyroglobulin conjugate mixed with 100 µg of murarnyl peptide, dissolved in phosphate buffered saline. Protocols for immunization and for the fusion of spleen cells from the immunized mice with cells of the non-secreting mouse SP2-O plasmacytoma line are described in detail, elsewhere (Milne R W. et al 1992, in Immunological Methods for Studying and Quantifying Lipoproteins and Apolipoproteins, Converse C A and Skinner E R eds, Oxford U Press, pp 61-84, which is incorporated herein by reference). Two methods of screening are used to identify specific antibodies in the culture supernatants of hybridomas. In the first protocol, an antigen, for example any one of $ANF_{1-25}$, $ANF_{74-98}$, $ANF_{99-126}$, $BNP_{1-25}$, $BNP_{52-76}$ (SEQ ID NO: 1), and $BNP_{77-108}$, is adsorbed to polystyrene Removal Wells (Dynatech) and after washing and saturation of the wells, they are successively exposed to hybridoma culture supernatant and $^{125}I$-anti-mouse IgG. In the second protocol, wells are coated with affinity-purified, anti-mouse IgG and then successively exposed to hybridoma culture supernatant and to a radiolabelled antigen, for example, but not limited to, $^{125}I$-$BNP_{52-76}$(SEQ ID NO:1), as appropriate. Details of the two screening protocols have been reported along with a discussion of their relative merits (Milne R W. et al 1992, in Immunological Methods for Studying and Quantifying Lipoproteins and Apolipoproteins, Converse C A and Skinner E R eds, Oxford U Press, pp 61-84, which is incorporated herein by reference).

Production of Polyclonal Antibodies

Immunization was carried out using a peptide-limpet hemocyanin conjugates prepared using Imject Maleimide Activated mcKLH or EDC Conjugation Kits obtained from The Pierce Chemical Company, (Rockford, Ill.). The peptide conjugates was emulsified in twice their volume with complete Freund's adjuvant (Difco Laboratories, Detroit, Mich.). Three-month-old New Zealand white rabbits were immunized by injecting the emulsion intradermally at several sites, so that each animal received a total of 3 mL of the emulsion. At a separate site 0.5 mL of crude *Bordetella pertussis* vaccine (Institut Armand-Frappier, Laval, Quebec) was injected intradermally. Animals were boosted with the conjugate emulsified with Freund's incomplete adjuvant at 4-week intervals and bled 10-14 days after each booster injection by ear vein puncture. Serum was aliquoted and stored at –70° C.

Preparation of Radiolabelled Tracer Peptides

Peptides were radioiodinated by a modification of the chloramine T method of Hunter and Greenwood or using the Bolton-Hunter reagent (Amersham Laboratories, Missisauga, Ontario). Ten µg of peptide in 10 µL of $H_2O$ was mixed with the appropriate reaction mixture. The reactions were stopped by the addition of 100 µL of 0.1% TFA. The diluted reaction mixture was quickly aspirated through a C18 Sep-Pak cartridge which had been previously wetted with 5 mL of 80% acetonitrile containing 0.1% TFA and with 5 mL of 0.1%, TFA. The cartridge was washed by aspirating 20 mL of 0.1% TFA and then eluted with 3 mL 80% acetonitrile containing 0.1% TFA. This eluate was evaporated at room temperature to one-third of its initial volume under nitrogen and immediately purified by reverse phase high performance liquid chromatography using a Vydac C,n column and a 60-min gradient of 8-35% acetonitrile containing 0.1% TFA at a flow rate of 1.5 mL/min.

Radioimmunoassays (RIA) Procedure

The buffer used for RIA was 0.1 M potassium phosphate (pH 7.4) containing 0.9% NaCl, 0.01% sodium azide and 0.1%1 heat-treated BSA. Polystyrene tubes (12×75 mm) were used for the reaction. All reagents were made in the RIA buffer. One hundred µL of standard solution of peptide or sample and 100 µL of a dilution of the appropriate antisera were incubated for 24 h at 4° C. After 24 h, 100 µL of labeled peptide (8000 dpm) was added. The mixture was further incubated for 24 h at 4° C.

Free and bound fractions were separated by adding goat anti-rabbit gamma globulin (Bio-Rad Laboratories, Mississauga, Ontario) and 100 µL of 5% normal rabbit serum. The mixture was incubated overnight at 4° C., after which 2 mL RIA buffer was added. The tubes were then centrifuged at 4000 g at 4° C. for 20 min. The supernatants were discarded and the precipitate was counted for radioactivity.

Samples for BNP Determination

Two 10 mL blood samples are collected per patient. The blood is centrifuged immediately at 4° C. and the plasma kept at –80° C. One sample is extracted as described below, for determination of $ANF_{99-126}$ and $BNP_{77-108}$. The plasma of the second tube is used for analysis using assays for proBNP fragments ($BNP_{1-25}$ and $BNP_{52-76}$ (SEQ ID NO:1)) and proANF fragments ($ANF_{1-25}$ and $ANF_{74-98}$).

Blood Collection

Blood (10 mL) was collected in tubes containing 10 mg EDTA and 1000 KIU of aprotinin (TRASYLOL, Miles Laboratories, Rexdale, Ontario). Plasma was immediately separated by centrifugation at 1000 g for 20 min at 4° C. and stored at –70° C. until assayed. Plasma samples were assayed after extraction using Sep-Pak cartridges as follows:

One to three mL were acidified by the addition of 100 µL/mL of 1N HCl and passed twice through a cartridge which had been previously wetted by passing 5 mL of 80% acetonitrile containing 0.1% TFA followed by 5 mL of 0.1% TFA. The cartridge with the adsorbed peptide was washed with 20 mL of 0.1% TFA and then eluted with 3 mL of 80% acetonitrile containing 0.1% TFA. The eluate was then lyophilized, dissolved in 100 µL of 20 mM HCl and 900 µL of RIA buffer and centrifuged for 15 min at 1000 g. Fifty to one hundred µL of the supernatant was used for RIA. Samples were assayed in duplicate. Stock solutions of 100 pg/mL of synthetic C I was prepared and stored in aliquots at −70° C. Dilutions containing from 30 to 5000 pg/mL of standard were made in RIA buffer.

Assay for N-Terminal (NT-) BNP

For the purposes of developing a simple method to measure NT-BNP, an ELISA protocol is pursued. Two approaches are possible for measuring soluble antigens with ELISAs: 1. Technology based on a direct competitive protocol, or, 2. Technology based on a "sandwich" technique involving a competitive reaction plus a reaction with a second antibody directed to a second epitope in the antigen. A capture and secondary polyclonal and monoclonal antibodies against the N-terminal portion of $BNP_{52-76}$ used is:
Lys-Ser-Arg-Glu-Val-Ala-Thr-Glu-Gly-Ile-Arg-Gly-His-His-Arg-Lys-Met-Val-Leu-Tyr-Thr-Leu-Arg-Ala-Pro-Arg
(SEQ ID NO:1)

The $BNP_{77-108}$ fragment may also be used (FIG. 1)

ANF was assayed in a similar manner as BNP, using the appropriate ANF antibodies, for example, $ANF_{99-126}$.

$BNP_{77-108}$ levels in patients exhibiting general non-chagasic cardiomyopathies, Chagas disease, Chagas disease and chagasic cardiomyopathy, Chagas disease also having conduction abnormalities within the heart, conduction abnormalities, and a control group are shown in FIG. 1.

These results indicate that patients infected with Chagas disease and also exhibiting chagasic cardiomyopathy show significantly elevated serum levels of BNP relative to all the other groups. Patients in the early stages of Chagas disease show slightly elevated BNP levels compared to the control group, yet these BNP levels are significantly reduced compared to the disease-infected and cardiomyopathy-exhibiting group. Patients exhibiting general cardiomyopathies or non-chagasic cardiomyopathies also display an elevated serum BNP level, however, these levels are much lower than the BNP levels of patients infected with Chagas disease and exhibiting chagasic cardiomyopathy.

Relative levels of $ANF_{99-126}$ circulating in patients exhibiting general nonchagasic cardiomyopathies, Chagas disease, Chagas disease and chagasic cardiomyopathy, Chagas disease also having conduction abnormalities within the heart, conduction abnormalities, and a control group are shown in FIG. 2. Patients displaying nonchagasic cardiomyopathies have elevated serum levels of $ANF_{99-126}$ relative to the control group. Patients infected with Chagas disease show similar serum levels of $ANF_{99-126}$ to the control group while patients with Chagas disease and chagasic cardiomyopathy display elevated levels compared to the control group. Similarly patients exhibiting Chagas disease plus conduction abnormalities or conduction abnormalities alone also display higher levels of $ANF_{99-126}$ compared to the control group.

Collectively, this data demonstrate that BNP, ANF, or both BNP and ANF levels may be used to aid in the prediction, detection, and monitoring of cardiomyopathy and myocarditis in patients exhibiting symptoms associated with infection. BNP levels may be a more sensitive indicator than ANF, however, ANF levels may be useful in combination with BNP levels to provide additional information regarding the disease state and may make it possible to make more accurate predictions or diagnoses. Furthermore, both the levels of ANF and BNP may be assayed simultaneously to provide for more refined monitoring of the disease and its symptoms.

Statistical Analysis

All results are expressed as mean±standard error of the means. Statistical significance of differences between means was tested using a non-paired student's "t" test or ANOVA (one-way analysis of variance).

Other methods of statistical analysis can also be applied, for example, Correlation analysis with posthoc test for statistical significance are carried out between continuous variables using standard procedures. Multivariate analysis (SYSTAT, an SPSS statistical package) is used to examine the independent predictive value of BNP values versus other risk factors including age, disease, sex, etc. Receiver-operating analysis is carried out to determine the relationship between sensitivity and specificity of BNP plasma values at different diagnostic cutoff values.

All publications referred to herein are incorporated by reference.

The present invention has been described with regard to preferred embodiments. However, it will be obvious to persons skilled in the art that a number of variations and modifications can be made without departing from the scope of the invention as described herein.

What is claimed is:

1. A method of predicting whether a human patient is susceptible to myocarditis resulting from an infection, the method comprising: obtaining a sample of a body fluid from the patient, assaying to determine a level of a brain natriuretic peptide (BNP), or both BNP and atrial natriuretic peptide (ANF), within the sample of body fluid and comparing the level of BNP, or both BNP and ANF to the level of BNP, or both BNP and ANF from a control group, wherein an increase in the level of BNP, or both BNP and ANF in the sample, compared to the level of BNP, or both BNP and ANF in the control group, indicates that myocarditis will arise as a result of an infection in the patient, and predicting the patient is susceptible to myocarditis as a result of the infection where the level of BNP, or both BNP and ANF in the sample is increased.

2. The method of claim 1 wherein the step of assaying to determine the level of BNP, or both BNP and ANF comprises performing an assay comprising at least one antibody exhibiting affinity for the BNP, ANF, or both.

3. The method of claim 1 wherein the body fluid comprises plasma.

4. The method of claim 1 wherein the body fluid comprises urine.

5. The method of claim 1 wherein the body fluid comprises cerebrospinal fluid.

6. The method of claim 1 wherein the infection comprises a viral infection, a rickettsial infection, a bacterial infection, a mycobacterial infection, a spirochetal infection, a fungal infection, or a parasitic infection.

7. The method of claim 6 wherein the parasitic infection comprises *Trypanosoma cruzi*.

8. The method of claim 2 wherein the at least one antibody comprises a polyclonal antibody, a monoclonal antibody, or a combination thereof.

9. The method of claim 8 wherein the at least one antibody comprises a polyclonal antibody.

10. The method of claim 8 wherein the at least one antibody comprises a monoclonal antibody.

11. The method of claim 2 wherein the step of obtaining a sample of a body fluid from the patient comprises obtaining two or more samples of body fluid from the patient at different points in time.

12. The method of claim 11 wherein, in the step of assaying to determine the level of BNP or the level of BNP and ANF, the level of BNP or the level of BNP and ANF is assayed within each of the two or more samples of body fluid, and the level of BNP or both BNP and ANF compared to determine a change in the BNP, or both BNP and ANF levels within the body fluid over time.

13. The method of claim 11, wherein a significant increase in the level of BNP, or both BNP and ANF is a predictor of myocarditis.

14. The method of claim 2 wherein the assay is selected from the group consisting of RIA, ELISA, fluoroimmunoassay, immunofluorometric assay, and immunoradiometric assay.

15. The method of claim 1, wherein the method further comprises treating the patient to treat myocarditis if the patient is predicted to be susceptible to myocarditis as a result of the infection.

16. The method of claim 1, wherein the human patient does not show signs of heart disease or dysfunction.

17. A method of assisting in the diagnosis of myocarditis that arises as a result of an infection in a human patient, the method comprising: obtaining a sample of a body fluid from the patient, assaying to determine a level of a brain natriuretic peptide (BNP), or both BNP and atrial natriuretic peptide (ANF), within the sample of body fluid and comparing the level of BNP, or both BNP and ANF to the level of BNP, or both BNP and ANF from a control group, wherein an increase in the level of BNP, or both BNP and ANF in the sample, compared to the level of BNP, or both BNP and ANF in the control group, is an indicator of myocarditis that arises as a result of an infection in a patient, and diagnosing myocarditis or the risk of myocarditis as a result of the infection where the level of BNP, or both BNP and ANF in the sample is increased.

18. The method of claim 17 wherein the step of assaying to determine the level of BNP, or both BNP and ANF comprises performing an assay comprising at least one antibody exhibiting affinity for the BNP, ANF, or both, and wherein the assay is selected from the group consisting of RIA, ELISA, fluoroimmunoassay, immunofluorometric assay, and immunoradiometric assay.

19. The method of claim 17, wherein the step of obtaining a sample of a body fluid from the patient comprises obtaining two or more samples of body fluid from the patient at different points in time, and wherein the body fluid comprises plasma.

* * * * *